(12) United States Patent
Kelly et al.

(10) Patent No.: US 11,918,725 B2
(45) Date of Patent: Mar. 5, 2024

(54) DUAL LUMEN CANNULA

(71) Applicant: CardiacAssist, Inc., Pittsburgh, PA (US)

(72) Inventors: Patrick A. Kelly, North Huntingdon, PA (US); Patrick E. Lutz, Pittsburgh, PA (US); Robert G. Svitek, Freeport, PA (US); Jerry Stokes, Sarver, PA (US)

(73) Assignee: CardiacAssist, Inc., Pittsburgh, PA (US)

( * ) Notice: Subject to any disclaimer, the term of this patent is extended or adjusted under 35 U.S.C. 154(b) by 0 days.

(21) Appl. No.: 17/518,224

(22) Filed: Nov. 3, 2021

(65) Prior Publication Data

US 2022/0054730 A1    Feb. 24, 2022

Related U.S. Application Data

(63) Continuation of application No. 16/404,317, filed on May 6, 2019, now Pat. No. 11,179,510, which is a continuation of application No. 15/720,005, filed on Sep. 29, 2017, now Pat. No. 10,279,101, which is a continuation of application No. 14/869,506, filed on Sep. 29, 2015, now Pat. No. 9,782,534, which is a
(Continued)

(51) Int. Cl.
| | |
|---|---|
| *A61M 1/36* | (2006.01) |
| *A61M 25/00* | (2006.01) |
| *A61M 60/13* | (2021.01) |
| *A61M 60/165* | (2021.01) |
| *A61M 60/38* | (2021.01) |
| *A61M 60/859* | (2021.01) |
| *A61M 60/113* | (2021.01) |

(52) U.S. Cl.
CPC ...... *A61M 1/3659* (2014.02); *A61M 25/0026* (2013.01); *A61M 25/0029* (2013.01); *A61M 25/007* (2013.01); *A61M 60/13* (2021.01); *A61M 60/165* (2021.01); *A61M 60/38* (2021.01); *A61M 60/859* (2021.01); *A61M 2025/0031* (2013.01); *A61M 2025/0039* (2013.01); *A61M 25/005* (2013.01); *A61M 60/113* (2021.01)

(58) Field of Classification Search
None
See application file for complete search history.

(56) References Cited

U.S. PATENT DOCUMENTS

| | | |
|---|---|---|
| 3,851,646 A | 12/1974 | Sarns |
| 3,902,492 A | 9/1975 | Greenhalgh |
| (Continued) | | |

*Primary Examiner* — Ankit D Tejani
(74) *Attorney, Agent, or Firm* — Seager, Tufte & Wickhem LLP

(57) ABSTRACT

A dual lumen coaxial cannula, assembly includes a first infusion tube having a first elongate body defining a first lumen therethrough and a second drainage tube co-axially aligned with the first infusion tube and having a second elongate body with a second lumen defined by a space between the first infusion tube and second drainage tube. A connector is removably attached to the first infusion tube and the second drainage tube for coupling the dual lumen coaxial cannula to an extracorporeal blood circuit. The first infusion tube and the second drainage tube include a plurality of infusion and drainage apertures, respectively, provided at the distal end and extending through the sidewall of the first infusion tube and the drainage tube, respectively.

17 Claims, 8 Drawing Sheets

Related U.S. Application Data continuation of application No. 13/718,110, filed on Dec. 18, 2012, now Pat. No. 9,168,352.

(60) Provisional application No. 61/577,257, filed on Dec. 19, 2011.

(56) References Cited

U.S. PATENT DOCUMENTS

| | | |
|---|---|---|
| 4,248,224 A | 2/1981 | Jones |
| 4,309,994 A | 1/1982 | Grunwald |
| 4,804,359 A | 2/1989 | Grunwald et al. |
| 5,476,453 A | 12/1995 | Mehta |
| 5,584,803 A | 12/1996 | Stevens et al. |
| 5,609,627 A | 3/1997 | Goicoechea et al. |
| 5,613,980 A | 3/1997 | Chauhan |
| 5,702,368 A | 12/1997 | Stevens et al. |
| 5,720,735 A | 2/1998 | Dorros |
| 5,769,812 A | 6/1998 | Stevens et al. |
| 5,785,686 A | 7/1998 | Runge |
| 5,792,094 A | 8/1998 | Stevens |
| 5,885,238 A | 3/1999 | Stevens et al. |
| 5,916,193 A | 6/1999 | Stevens et al. |
| 5,928,181 A | 7/1999 | Coleman et al. |
| 5,957,879 A | 9/1999 | Roberts et al. |
| 6,110,145 A | 8/2000 | Macoviak |
| 6,117,117 A | 9/2000 | Mauch |
| 6,152,141 A | 11/2000 | Stevens et al. |
| 6,161,547 A | 12/2000 | Barbut |
| 6,190,357 B1 | 2/2001 | Ferrari et al. |
| 6,210,363 B1 | 4/2001 | Esch et al. |
| 6,210,380 B1 | 4/2001 | Mauch |
| 6,258,073 B1 | 7/2001 | Mauch |
| 6,267,751 B1 | 7/2001 | Mangosong |
| 6,432,136 B1 | 8/2002 | Weiss et al. |
| 6,461,327 B1 | 10/2002 | Addis et al. |
| 6,475,208 B2 | 11/2002 | Mauch |
| 6,494,875 B1 | 12/2002 | Mauch |
| 6,508,777 B1 | 1/2003 | Macoviak et al. |
| 6,582,388 B1 | 6/2003 | Coleman et al. |
| 6,673,040 B1 | 1/2004 | Samson et al. |
| 6,682,499 B2 | 1/2004 | Lenker |
| 6,692,473 B2 | 2/2004 | St. Cyr et al. |
| 6,726,651 B1 | 4/2004 | Robinson et al. |
| 6,758,836 B2 | 7/2004 | Zawacki |
| 6,814,713 B2 | 11/2004 | Aboul-Hosn et al. |
| 6,837,864 B1 | 1/2005 | Bertolero et al. |
| 6,878,140 B2 | 4/2005 | Barbut |
| 6,889,713 B2 | 5/2005 | Navis |
| 6,902,556 B2 | 6/2005 | Grimes et al. |
| 6,913,601 B2 | 7/2005 | St. Goar et al. |
| 7,022,100 B1 | 4/2006 | Aboul-Hosn et al. |
| 7,025,756 B2 | 4/2006 | Frazier et al. |
| 7,090,659 B2 | 8/2006 | Aboul-Hosn et al. |
| 7,229,429 B2 | 6/2007 | Martin et al. |
| 7,276,043 B2 | 10/2007 | Heath et al. |
| 7,445,592 B2 | 11/2008 | Pecor |
| 7,473,239 B2 | 1/2009 | Wang et al. |
| 7,513,863 B2 | 4/2009 | Bolling et al. |
| 7,569,029 B2 | 8/2009 | Clark |
| 7,575,563 B2 | 8/2009 | Appling |
| 7,604,621 B2 | 10/2009 | Eidenschink |
| 7,766,853 B2 | 8/2010 | Lane |
| 7,785,246 B2 | 8/2010 | Aboul-Hosn et al. |
| 7,819,856 B2 | 10/2010 | Bates |
| 7,824,357 B2 | 11/2010 | Al-Rashdan |
| 7,875,017 B2 | 1/2011 | Sabbah |
| 7,879,003 B2 | 2/2011 | Bertolero et al. |
| 7,896,832 B2 | 3/2011 | Zafirelis et al. |
| 7,935,102 B2 | 5/2011 | Breznock et al. |
| 7,981,093 B2 | 7/2011 | Schon et al. |
| 8,029,457 B2 | 10/2011 | Ash et al. |
| 8,231,519 B2 | 7/2012 | Reichenbach et al. |
| 9,782,534 B2 | 10/2017 | Kelly et al. |
| 10,279,101 B2 | 5/2019 | Kelly et al. |
| 2003/0004452 A1 | 1/2003 | Lenker |
| 2003/0138350 A1 | 7/2003 | Macoviak et al. |
| 2004/0171997 A1 | 9/2004 | Wilson et al. |
| 2005/0054990 A1 | 3/2005 | Graft et al. |
| 2005/0096609 A1 | 5/2005 | Maginot et al. |
| 2005/0277862 A1 | 12/2005 | Anand |
| 2005/0279370 A1 | 12/2005 | Aboul-Hosn et al. |
| 2006/0149187 A1 | 7/2006 | Bertolero et al. |
| 2006/0184098 A1 | 8/2006 | Barnitz et al. |
| 2007/0106247 A1 | 5/2007 | Burnett et al. |
| 2007/0129704 A1 | 6/2007 | O'Mahony et al. |
| 2007/0167925 A1 | 7/2007 | Jacqmein |
| 2007/0197998 A1 | 8/2007 | Itou et al. |
| 2008/0021417 A1 | 1/2008 | Zawacki et al. |
| 2008/0108975 A1 | 5/2008 | Appling et al. |
| 2008/0215018 A1 | 9/2008 | Duffy et al. |
| 2009/0005725 A1 | 1/2009 | Shorey |
| 2009/0069792 A1 | 3/2009 | Frey et al. |
| 2009/0076482 A1 | 3/2009 | Jonkman |
| 2009/0088699 A1 | 4/2009 | King et al. |
| 2009/0124968 A1 | 5/2009 | Goshgarian |
| 2009/0163864 A1 | 6/2009 | Breznock et al. |
| 2009/0204083 A1 | 8/2009 | O'Donnell et al. |
| 2009/0247927 A1 | 10/2009 | Clark |
| 2009/0247987 A1 | 10/2009 | Chevalier, Jr. et al. |
| 2009/0312702 A1 | 12/2009 | Holman et al. |
| 2010/0004594 A1 | 1/2010 | Eidenschink |
| 2010/0010442 A1 | 1/2010 | Shivkumar et al. |
| 2010/0057020 A1 | 3/2010 | Uretsky |
| 2010/0233282 A1 | 9/2010 | Mishra |
| 2011/0040241 A1 | 2/2011 | Wang et al. |
| 2011/0190683 A1 | 8/2011 | Gellman et al. |
| 2011/0245665 A1 | 10/2011 | Nentwick |
| 2011/0313341 A1 | 12/2011 | Kassab |
| 2011/0313401 A1 | 12/2011 | Ash et al. |
| 2012/0165788 A1 | 6/2012 | Burnett et al. |

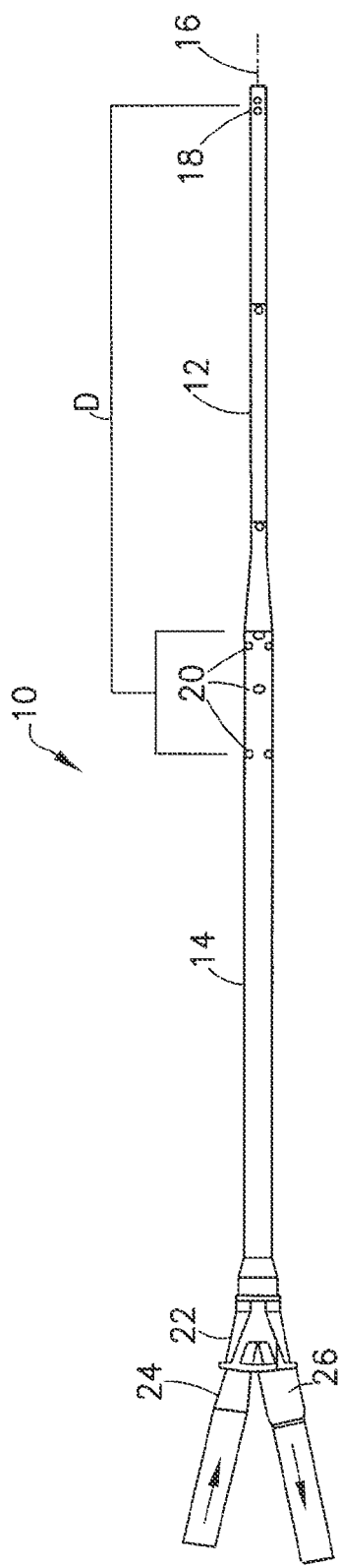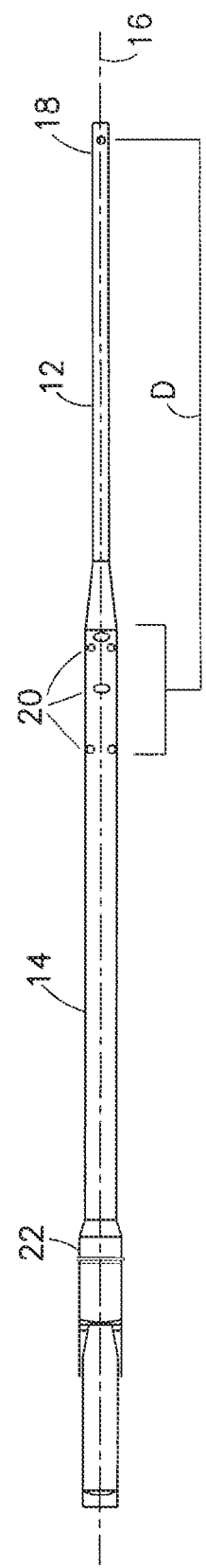

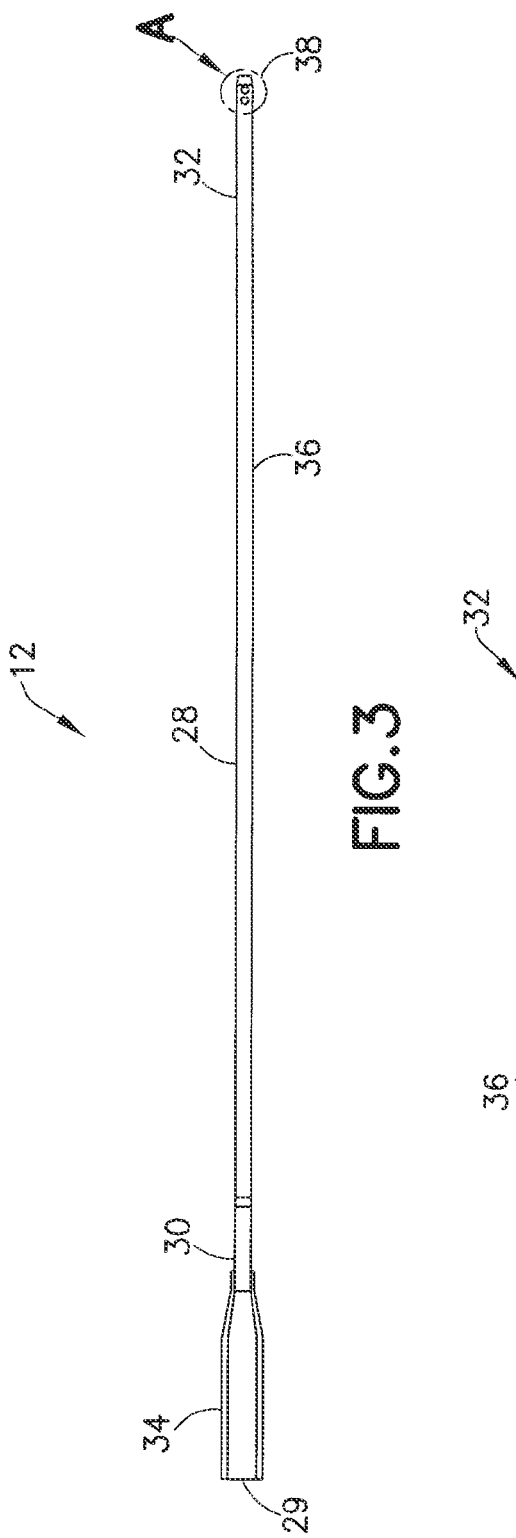
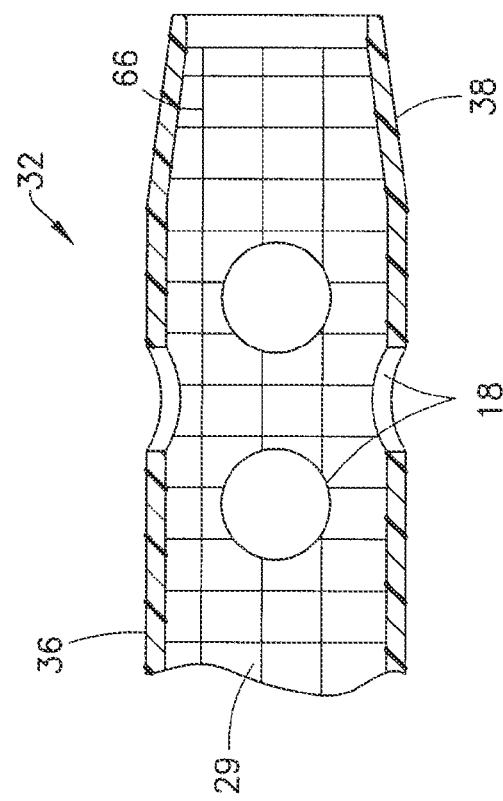

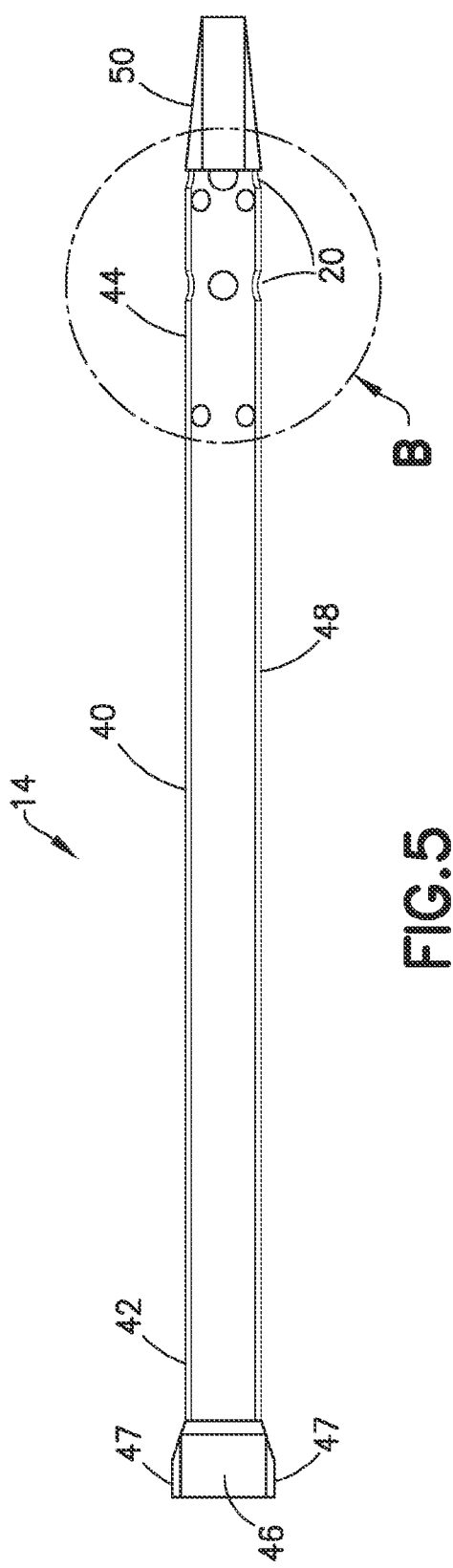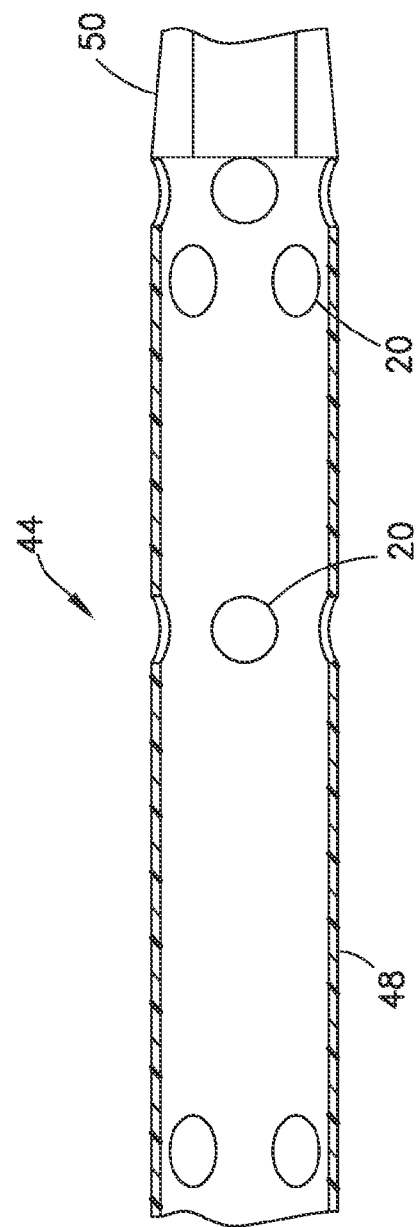

DUAL LUMEN CANNULA

CROSS-REFERENCE TO RELATED APPLICATIONS

The present application is a continuation application of U.S. application Ser. No. 16/404,317, filed May 6, 2017, which is a continuation application of U.S. patent application Ser. No. 15/720,005, filed Sep. 29, 2017, now U.S. Pat. No. 10,279,101, which is a continuation application of U.S. patent application Ser. No. 14/869,506, filed Sep. 29, 2015, now U.S. Pat. No. 9,782,534, which is a continuation application of U.S. patent application Ser. No. 13/718,110, filed Dec. 18, 2012, now U.S. Pat. No. 9,168,352, which claims priority to U.S. Provisional Patent Application No. 61/577,257, filed Dec. 19, 2011, entitled "Dual Lumen Cannula", the entire disclosures of which are incorporated by reference herein.

BACKGROUND OF THE INVENTION

Field of the Invention

The present invention relates, in general, to devices and methods for assisting a patient's heart with a cannula. More specifically, the present invention is related to devices and methods for assisting a patient's heart with a cannula where the cannula is of sufficient length to, for example, extend from the patient's internal jugular vein to the pulmonary artery.

Description of the Related Art

Traditional cannulae used for patient life support generally involve single lumen cannulae at multiple insertion sites, high volume circuits, and cannulae that are not capable of long-term use. Multiple insertion sites increase the risk of bleeding, vessel damage, infection, as well as pain and discomfort to the patient. These cannulae are designed and built for short-term acute therapies. Additionally, traditional cannulae usually require access sites located in the patient's groin area near the right or left femoral veins.

Patients with severe right-sided circulatory and/or right-sided ventricular failure have significantly high mortality and morbidity caused by a multitude of factors in multiple patient populations. Historically, Right Ventricular Assist Devices (RVADs) and Left Ventricular Assist Devices (LVADs) have been adapted for use on surgical patients without a percutaneous or catheter lab option available. These surgical RVADs have been applied on patients with right inferior myocardial infarction, acute right-sided ischemic myocardial infarctions (with large left and right propagation), cardiogenic shock, LVAD-created right ventricular dysfunction, post-transplant right ventricular failure, and pulmonary hypertension. Acute myocardial infarction and cardiogenic shock have been treated with intra-aortic balloon pumps and maximal inotropic support, to which many patients become refractory. Surgically implanted LVADs can create a significant septal shift that leads to a dynamic change in the Starling curve that abruptly places patients into severe right ventricular failure. Patients can limit post-transplant survival bridged to transplant to/from an RVAD with severe right ventricular failure. Secondary pulmonary hypertension leads to an exacerbation of right ventricular failure in acute and chronic situations, which may be treated with RVADs.

The foregoing conventional devices do not have the capability to reach the pulmonary artery (PA) from the internal jugular vein via a percutaneous insertion. Some traditional cannulae are inserted into the patient's heart through a direct access point in the patient's right or left femoral vein. Alternatively, traditional RVADs have a cannula either primarily placed in the PA or a graft sewn onto the PA, then a cannula inserted through the graft. The assembly can then be visualized in the PA via fluoroscopy and X-Ray with the aid of distal markers in the cannula, verifying the proper orientation of the outflow to the patient. In these embodiments, the patient's torso length can limit the ability to access the PA via percutaneous insertion. If a cannula is not of a proper length, the interventional procedure may not unload the right ventricle, which leads to an increase of morbidity and mortality.

Furthermore, traditional venoarterial extracorporeal membrane oxygenation (VA ECMO) is the current standard of care used to treat right ventricular failure and respiratory failure percutaneously. VA ECMO procedure draws blood from the right atrium and pumps it through an oxygenator and back into the arterial circulation via the femoral artery. VA ECMO bypasses the lungs and the heart completely. Therefore, residual blood is left stagnant in both the heart and lungs potentially leading to thrombosis and an inadequately unloaded right ventricle. Additionally, the arterial cannulation can lead to problems including but not limited to bleeding, stroke, and infection.

SUMMARY OF THE INVENTION

In view of the foregoing, there is a need for a dual lumen cannula with a single insertion point. There is an additional need for a dual lumen cannula that eliminates multiple access sites, reduces bleeding, vessel damage, and infection, as well as pain and discomfort to the patient. Furthermore, there exists a need for a dual lumen cannula that enables patients to be ambulatory with access sites provided in the neck area instead of the groin.

In one embodiment, a dual lumen coaxial cannula assembly includes a first infusion tube having a first elongate body defining a first lumen therethrough and a second drainage tube co-axially aligned with the infusion tube and having a second elongate body with a second lumen defined by a space between the first infusion tube and second drainage tube. The first infusion tube may have a proximal end, a distal end, and a sidewall extending circumferentially therebetween. A first connector portion may be provided at the proximal end of the first infusion tube for coupling the first insertion tube to a connector. The second drainage tube may have a proximal end, a distal end, and a sidewall extending circumferentially therebetween. A second connector portion may be provided at the proximal end of the second drainage tube for coupling the second drainage tube to the connector. In accordance with another embodiment, a connector may be removably attached to the first connector portion and the second connector portion for coupling the first infusion tube and the second drainage tube to an extracorporeal blood circuit.

According to another embodiment, the first infusion tube may include a plurality of infusion apertures provided at the distal end. The infusion apertures may extend through the sidewall of the first infusion tube. Similarly, the second drainage tube may include a plurality of drainage apertures provided at the distal end, the drainage apertures extending through the sidewall of the second drainage tube. The plurality of infusion apertures may extend through the sidewall of the first infusion tube in a direction perpendicular to a longitudinal axis of the first infusion tube. In a similar manner, the plurality of drainage apertures may extend through the sidewall of the second drainage tube in a direction perpendicular to a longitudinal axis of the second drainage tube. Alternatively, the plurality of infusion apertures may extend through the sidewall of the first infusion tube at an acute or obtuse angle with respect to a longitudinal axis of the first infusion tube. Similarly, the plurality of infusion apertures extends through the sidewall of the first infusion tube at an acute or obtuse angle with respect to a longitudinal axis of the first infusion tube.

In another embodiment, a wire mesh basket is provided inside the first lumen at a location surrounding the plurality of infusion apertures for supporting and preventing collapse of the sidewall of the first infusion tube. In a similar manner, a wire mesh basket is provided inside the second lumen at a location surrounding the plurality of drainage apertures for supporting and preventing collapse of the sidewall of the second drainage tube. A reinforcing coil may extend from the proximal end to the distal end of one or both of the first infusion tube and the second drainage tube. The reinforcing coil desirably extends in a helical manner along the length of one or both of the first infusion tube and the second drainage tube.

In accordance with another embodiment, the connector may further include a distal aperture in fluid communication with an inlet portion and an outlet portion, and a barbed fitting on the inlet portion and the outlet portion for connecting an infusion line and a drainage line to the connector. The dual lumen coaxial cannula may be adapted for inserting into an internal jugular vein of a patient. In another embodiment, the dual lumen coaxial cannula may be adapted for maneuvering through the patient's vasculature such that the first distal end of the first infusion cannula is at least within proximity of the patient's pulmonary artery and such that the second distal end of the second drainage cannula is at least within proximity of the patient's right atrium.

According to a further embodiment, a method of assisting a patient's heart may include the step of providing a dual lumen coaxial cannula assembly having a first infusion tube having a first elongate body defining a first lumen therethrough and a second drainage tube coaxially aligned with the infusion tube and having a second elongate body with a second lumen defined by a space between the first infusion tube and second drainage tube. The first infusion tube may have a proximal end, a distal end, and a sidewall extending circumferentially therebetween. A first connector portion may be provided at the proximal end of the first infusion tube for coupling the first insertion tube to a connector. The second drainage tube may have a proximal end, a distal end, and a sidewall extending circumferentially therebetween. A second connector portion may be provided at the proximal end of the second drainage tube for coupling the second drainage tube to the connector. In accordance with another embodiment, a connector may be removably attached to the first connector portion and the second connector portion for coupling the first infusion tube and the second drainage tube to an extracorporeal blood circuit. The method may further include the step of inserting the dual lumen coaxial cannula into an internal jugular vein of the patient, wherein the dual lumen coaxial cannula has a length to extend from the patient's neck area to the patient's heart. The method may also include the step of maneuvering the dual lumen coaxial cannula through the patient's vasculature such that the first distal end of the first infusion cannula is at least within proximity of the patient's pulmonary artery and such that the second distal end of the second drainage cannula is at least within proximity of the patient's right atrium. In another embodiment, the method may also include the steps of connecting the connector to a blood pump for establishing right ventricular support and inserting a guidewire to guide the dual lumen coaxial cannula during the maneuvering step. Blood from the blood pump may be delivered to the patient's pulmonary artery through the plurality of infusion apertures of the first infusion tube. Desirably, blood may be withdrawn from the patient's right atrium through the plurality of drainage apertures of the second drainage cannula.

Further details and advantages of the present invention will be understood from the following detailed description read in conjunction with the accompanying drawings.

BRIEF DESCRIPTION OF THE DRAWINGS

FIG. 1 is a top view of one embodiment of a coaxial cannula shown with a connector.

FIG. 2 is a side view of the coaxial cannula shown in FIG. 1.

FIG. 3 is a top view of one embodiment of an infusion cannula.

FIG. 4 is a cross-sectional view of detail A shown in FIG. 3.

FIG. 5 is a top view of one embodiment of a drainage cannula.

FIG. 6 is a cross-sectional view of detail B in FIG. 5.

DETAILED DESCRIPTION OF THE INVENTION

Figure 7:
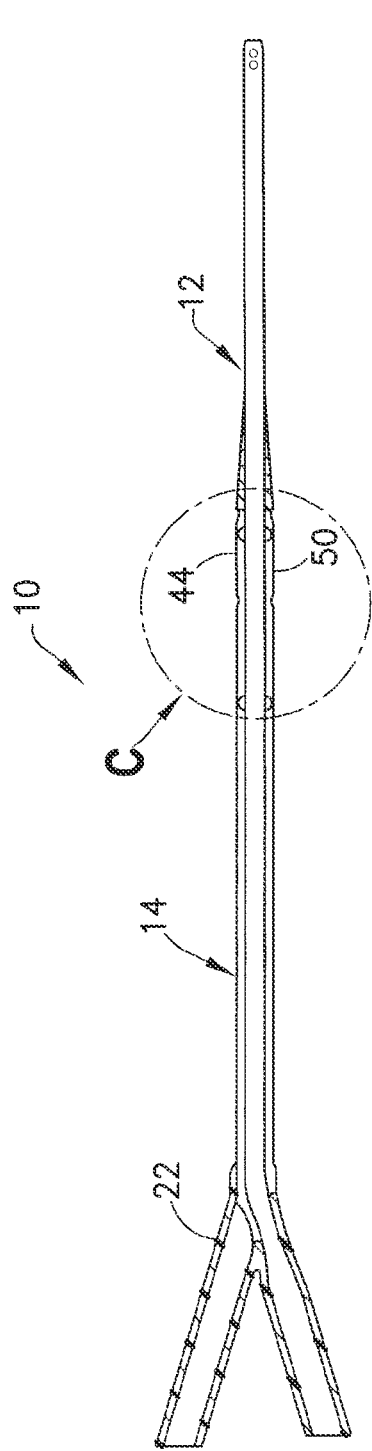
FIG. 7 is a top cross-sectional view of the coaxial cannula taken along line A-A in FIG. 2.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Referring to the drawings, in which like reference characters refer to like parts throughout the several views thereof, various embodiments of a coaxial, dual lumen cannula 10 (hereinafter referred to as "coaxial cannula 10") are shown. With initial reference to FIGS. 1-2, the assembled coaxial cannula 10, according to one embodiment, generally includes a first infusion tube 12 having a first length and a second drainage tube 14 having a second length. The first length of the first infusion tube 12 is greater than the second length of the second drainage tube 14.

The first infusion tube 12 is disposed within the second drainage tube 14 in a coaxial arrangement centered about a central axis 16. Each of the first infusion tube 12 and the second drainage tube 14 has a first circumference defining a first lumen and a second circumference defining a second lumen, respectively. The first circumference of the first infusion tube 12 is smaller than the second circumference of the second drainage tube 14 such that the first infusion tube 12 may be placed within the second lumen of the second drainage tube 14. One or both of the first infusion tube 12 and the second drainage tube 14 may be manufactured from a medical-grade material such as polyurethane. Alternatively, the tubes may be made from PVC or silicone, and may be dip molded, extruded, co-molded, or made using any other suitable manufacturing technique.

The coaxial cannula 10 has sufficient placement flexibility adapted for placement of the coaxial cannula 10 within a patient's body. Desirably, a vascular insertion site is provided at the internal jugular vein on the patient's neck area. The coaxial cannula 10 is adapted for placement above or below the right atrium of the patient's heart. The coaxial cannula 10 may be used with an introducer to guide the placement of the coaxial cannula 10 as it is inserted within the patient's body.

With continuing reference to FIGS. 1 and 2, the coaxial cannula 10 is designed to withdraw blood directly from the patient's heart and return blood back into the patient's heart. The function of the first infusion tube 12 is to deliver blood into the blood stream of the patient, while the function of the second drainage tube 14 is to drain the blood from the patient's bloodstream as will be described hereafter.

A plurality of infusion apertures 18 is provided at a distal end of the first infusion tube 12. The plurality of infusion apertures 18 is desirably arranged in a circular pattern extending around the outer circumference of the first infusion tube 12. In some embodiments, the plurality of infusion apertures 18 may be disposed in multiple groups provided at various sites on the first infusion tube 12. Similarly, the second drainage tube 14 includes a plurality of drainage apertures 20 provided at a distal end of the second drainage tube 14. The plurality of drainage apertures 20 is desirably arranged in a circular pattern extending around the outer circumference of the second drainage tube 14. In alternative embodiments, the plurality of drainage apertures 20 may be arranged in groups disposed at various sites along the length of the second drainage tube 14. The infusion apertures 18 are separated from the drainage apertures 20 by a distance D. In different embodiments of the coaxial cannula 10, the separation of infusion apertures 18 from drainage apertures 20 determines the amount of mixing of oxygenated blood and unoxygenated blood. This distance may vary based on the age and size of the patient, as well as the desired flow rates during the medical procedure where the coaxial cannula 10 is used. For example, a coaxial cannula 10 having a specific overall length and diameter, along with a desired pattern and distance between the infusion apertures 18 and the drainage apertures 20 may be selected based on age and/or size of the patient.

With continuing reference to FIGS. 1 and 2, a connector 22 is provided at the proximal end of the coaxial cannula 10. The connector 22 includes an inlet portion 24 in fluid communication with the first infusion tube 12 to transfer blood from a blood pump (not shown) to the first infusion tube 12. An outlet portion 26 of the connector 22 is in fluid communication with the second drainage tube 14 to transfer blood from the second drainage tube 14 to the blood pump. The outlet portion 26 and the inlet portion 24 of the connector 22 are arranged such that the fluid pathways leading from the second drainage tube 14 and to the first infusion tube 12 transition from a coaxial arrangement at a distal end of the connector 22 to an axially-offset arrangement at a proximal end of the connector 22. Details of the connector 22 construction will be discussed in greater detail below.

With reference to FIGS. 3-4, and with continuing reference to FIGS. 1 and 2, the first infusion tube 12 is illustrated separate from the coaxial cannula 10. The first infusion tube 12 has a first elongate body 28 having a working length of, for example, around 21 cm. The first elongate body 28 of the first infusion tube 12 is substantially cylindrical and extends from a first proximal end 30 to a first distal end 32. The first elongate body 28 includes a first lumen 29 extending throughout the entire length of the first infusion tube 12. The first proximal end 30 includes a first connector portion 34 for coupling the first infusion tube 12 to the inlet portion 24 of the connector 22. The first elongate body 28 of the first infusion tube 12 has a hollow structure defined by a first sidewall 36 extending circumferentially about the first elongate body 28. The first sidewall 36 has a substantially constant thickness throughout the length of the first elongate body 28, with a first tapering section 38 at the first distal end 32 of the first elongate body 28. At the first proximal end 30 of the first elongate body 28, the first sidewall 36 gradually increases in thickness before transitioning into the first connector portion 34. The first tapering section 38 located at the first distal end 32 has a thinner first sidewall 36 but retains the internal diameter of the first infusion tube 12. The first tapering section 38 enables easier insertion of the first infusion tube 12 into the patient's body.

With specific reference to FIG. 4, the first distal end 32 of the first infusion tube 12 is shown. The plurality of infusion apertures 18 is provided at the first distal end 32 of the first infusion tube 12. The plurality of infusion apertures 18 extends circumferentially around the first distal end 32. Each infusion aperture 18 has a diameter of, for example, about 1 mm. The plurality of infusion apertures 18 may be arranged in an alternating pattern of axially offset rows of infusion apertures 18 arranged around the circumference of the first infusion tube 12. Each of the plurality of infusion apertures 18 extends through the thickness of the first sidewall 36. The infusion apertures 18 illustrated in FIGS. 3 and 4 extend through the first sidewall 36 in a direction perpendicular to a longitudinal axis of the first elongate body 28. Alternatively, the plurality of infusion apertures 18 may extend through the thickness of the first sidewall 36 in an angled manner with respect to the longitudinal axis of the first elongate body 28. For example, the plurality of infusion apertures 18 may be arranged at an acute or obtuse angle with respect to a cross-sectional plane of the first infusion tube 12 extending perpendicular to the longitudinal axis of the first elongate body 28. In some embodiments, a wire mesh basket is provided inside the first lumen 29 of the first infusion tube 12 at a location surrounding the infusion apertures 18. The wire mesh basket supports and prevents the first sidewall 36 from collapsing due to being weakened by the formation of the plurality of infusion apertures 18. In one embodiment, one or more sensors (not shown) may be provided at first distal end 32 of the first infusion tube 12. The sensor(s) may be adapted for measuring, for example, local blood pressure and/or oxygen concentration.

The total cross-sectional area of the plurality of infusion apertures 18 is desirably approximately equal to or greater than the cross-sectional area of the first lumen 29. If the cross-sectional area of the plurality of infusion apertures 18 is less than the cross-sectional area of the first lumen 29, an undesirable pressure drop may occur. This pressure drop reduces the flow throughput within the first lumen 29 and impairs the efficiency of the first infusion tube 12. Desirably, the total cross sectional area of the plurality of infusion apertures 18 exceeds the cross sectional area of the first lumen 29 such that if one or more of the infusion apertures 18 becomes clogged, the total cross sectional area of the remaining infusion apertures 18 is equal to or greater than the cross sectional area of the first lumen 29. In this manner, the blood flow through the first lumen 29 is maximized even if one or more of the infusion apertures 18 become clogged.

With reference to FIGS. 5-6, and with continuing reference to FIGS. 1 and 2, the second drainage tube 14 is illustrated separate from the coaxial cannula 10. The second drainage tube 14 has a second elongate body 40 having a working length of, for example, around 12 cm. The second elongate body 40 of the second drainage tube 14 is substantially cylindrical and extends from a second proximal end 42 to a second distal end 44. The second elongate body 40 includes a second lumen 46 extending throughout the entire length of the second drainage tube 14. The second proximal end 42 includes a second connector portion 47 for coupling the second drainage tube 14 to the outlet portion 26 of the connector 22. The second elongate body 40 of the second drainage tube 14 has a hollow structure defined by a second sidewall 48 extending circumferentially about the second elongate body 40. The second sidewall 48 has a substantially constant thickness throughout the length of the second elongate body 40, with a second tapering section 50 at the second distal end 44 of the second elongate body 40. At the second proximal end 42 of the second elongate body 40, the second sidewall 48 gradually increases in thickness before transitioning into the second connector portion 47. The second tapering section 50 located at the second distal end 44 has a thinner second sidewall 48 but retains the internal diameter of the second lumen 46. The second tapering section 50 enables easier insertion of the second drainage tube 14 into the patient's body.

With specific reference to FIG. 6, the second distal end 44 of the second drainage tube 14 is shown. The plurality of drainage apertures 20 is provided at the second distal end 44 of the second drainage tube 14. The plurality of drainage apertures 20 extends circumferentially around the second distal end 44. Each drainage aperture 20 has a diameter of, for example, about 1.5 mm. The plurality of drainage apertures 20 may be arranged in an alternating pattern of axially offset rows around the circumference of the second drainage tube 14. Each of the plurality of drainage apertures 20 extends through the thickness of the second sidewall 48. The drainage apertures illustrated in FIGS. 5 and 6 extend through the second sidewall 48 in a direction perpendicular to a longitudinal axis of the second elongate body 40. Alternatively, the plurality of drainage apertures 20 may extend through the thickness of the second sidewall 48 in an angled manner with respect to the longitudinal axis of the second elongate body 40. For example, the plurality of drainage apertures 20 may be arranged at an acute or obtuse angle with respect to a cross-sectional plane of the second drainage tube 14 extending perpendicular to the longitudinal axis of the second elongate body 40. In some embodiments, a wire mesh basket is provided inside the second lumen 46 of the second drainage tube 14 at a location surrounding the drainage apertures 20. The wire mesh basket supports and prevents the second sidewall 48 from collapsing due to being weakened by the formation of the plurality of drainage apertures 20. In one embodiment, one or more sensors (not shown) may be provided at second distal end 44 of the second drainage tube 14. The sensor(s) may be adapted for measuring, for example, local blood pressure and/or oxygen concentration.

The total cross sectional area of the plurality of drainage apertures 20 is desirably approximately equal to or greater than the cross sectional area of the second lumen 46. If the cross sectional area of the plurality of drainage apertures 20 is less than the cross sectional area of the second lumen 46, an undesirable pressure drop within the second drainage tube 14 may occur. This pressure drop reduces the flow throughput within the second lumen 46 and impairs the efficiency of the second drainage tube 14. Desirably, the total cross sectional area of the plurality of drainage apertures 20 exceeds the cross sectional area of the second lumen 46 such that if one or more drainage apertures 20 becomes clogged, the total cross sectional area of the remaining drainage apertures 20 is equal to or greater than the cross sectional area of the second lumen 46. In this manner, the blood flow through the second lumen 46 is maximized even if one or more of the drainage apertures 20 becomes clogged.

Figure 8:
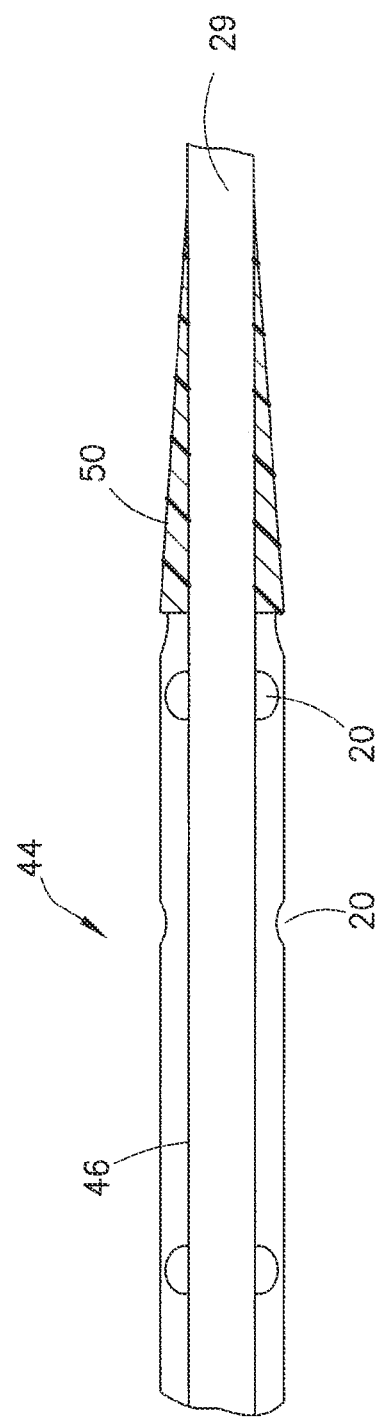
FIG. 8 is a cross-sectional view of detail C in FIG. 7, illustrating a transition portion at a distal end of a drainage cannula of the coaxial cannula.

With reference to FIG. 7, the coaxial cannula 10 shown in FIGS. 1 and 2 is illustrated in cross section. The second distal end 44 of the second drainage tube 14 is fixedly attached to a mid portion of the first infusion tube 12 along the length of second tapering section 50, as shown in FIG. 8. The first infusion tube 12 and the second drainage tube 14 are coupled to the connector 22 in such manner that the first infusion tube 12 and the second drainage tube 14 cross inside the connector 22 body without being connected to each other.

Figure 9:
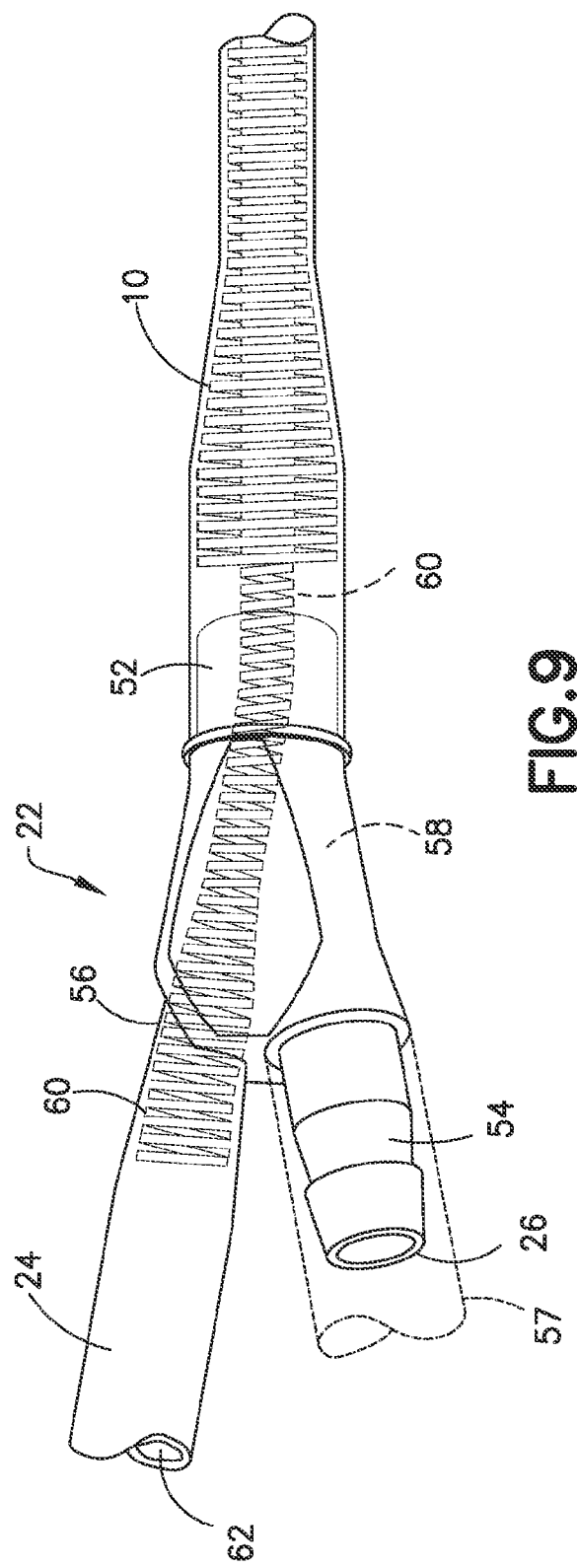
FIG. 9 is a perspective view of a connector shown coupled to a coaxial cannula according to another embodiment.
Figure 10:
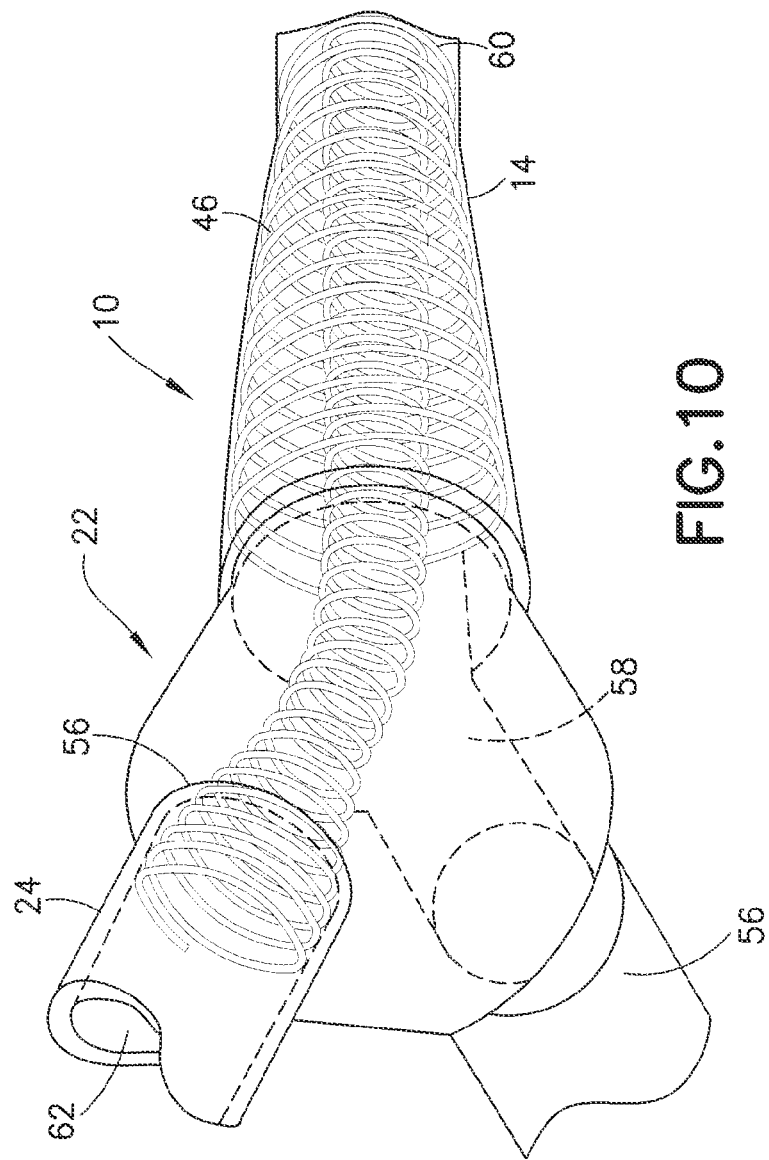
FIG. 10 is a rear perspective view of the coaxial cannula shown in FIG. 9.

With reference to FIGS. 9 and 10, a detailed view of the connector 22 is shown coupled to a coaxial cannula 10 according to another embodiment. FIG. 9 illustrates the connector 22 shows the fluid pathways extending through the interior of the connector 22. The connector includes a distal aperture 52 at a distal end of the connector 22 for connecting to the proximal end of the coaxial cannula 10. The proximal end of the connector 22 has the inlet portion 24 and the outlet portion 26 in fluid communication with the distal aperture 52. The outlet portion 26 may include a barbed fitting 54 for connecting a drainage connection 57 that extends to a blood pump. The inlet portion 24 includes an inner tube 56 that extends through the interior of the connector 22 and connects with the first infusion tube 12. The inner tube 56 may extend beyond the distal aperture 52 for connecting with the first infusion tube 12. A drainage opening 58 connects the second drainage tube 14 with the outlet portion 26 of the connector 22. The drainage opening 58 is coextensive with the inner tube 56 along the length of the body portion of the connector 22. The inner tube 56 may be reinforced with a metal or plastic coil 60 that extends in a helical manner along the length of the inner tube 56 to minimize kinking and/or collapse of the first infusion tube 12.

With continuing reference to FIGS. 9 and 10, the inner tube 56 passes through the connector 22 to provide a smooth, seamless transition from a single distal aperture 52 to the branched arrangement of the inlet portion 24 and the outlet portion 26. The transition is desirably void of any joints, welds, and other connections that can create irregularities in the flow of blood and can damage blood cells.

In use, the proximal end of the coaxial cannula 10 is connected to the distal aperture 52 of the connector 22. The inner tube 56 receives blood from a supply line 62 and sends it through the lumen of the inner tube 56 to the first infusion tube 12. As the diameter of the inner tube 56 is smaller than the diameter of the drainage opening 58, the inner tube 56 extends through the interior of the connector 22, thus allowing the inner tube 56 to be continuous throughout the length of the connector 22. Depending on the application, the inner tube 56 may or may not include structural reinforcement in the form of the coil 60. In embodiments where the inner tube 56 is reinforced with the coil 60, the inner tube 56 is stronger and less susceptible to kinking or collapse.

The connector 22 may be made from polycarbonate as an example, but could also be made from PVC, acrylic, or polyurethane. The connector 22 may be constructed using one or more manufacturing techniques including injection molding, machining, or dip forming. One of ordinary skill in the art will understand that a variety of other manufacturing techniques may be used for constructing the connector 22 without departing from the intended scope of the invention.

With continued reference to FIGS. 9 and 10, one or both of the first elongate body 28 of the first infusion tube 12 and the second elongate body 40 of the second drainage tube 14 includes a helical coil 60 extending through the length thereof. The helical coil 60 may be disposed along the interior surface of the first lumen 29 and the second lumen 46. Alternatively, the helical coil 60 may be disposed within the first sidewall 36 and the second sidewall 48. The helical coil 60 may be manufactured from medical grade metal or plastic.

Figure 11:
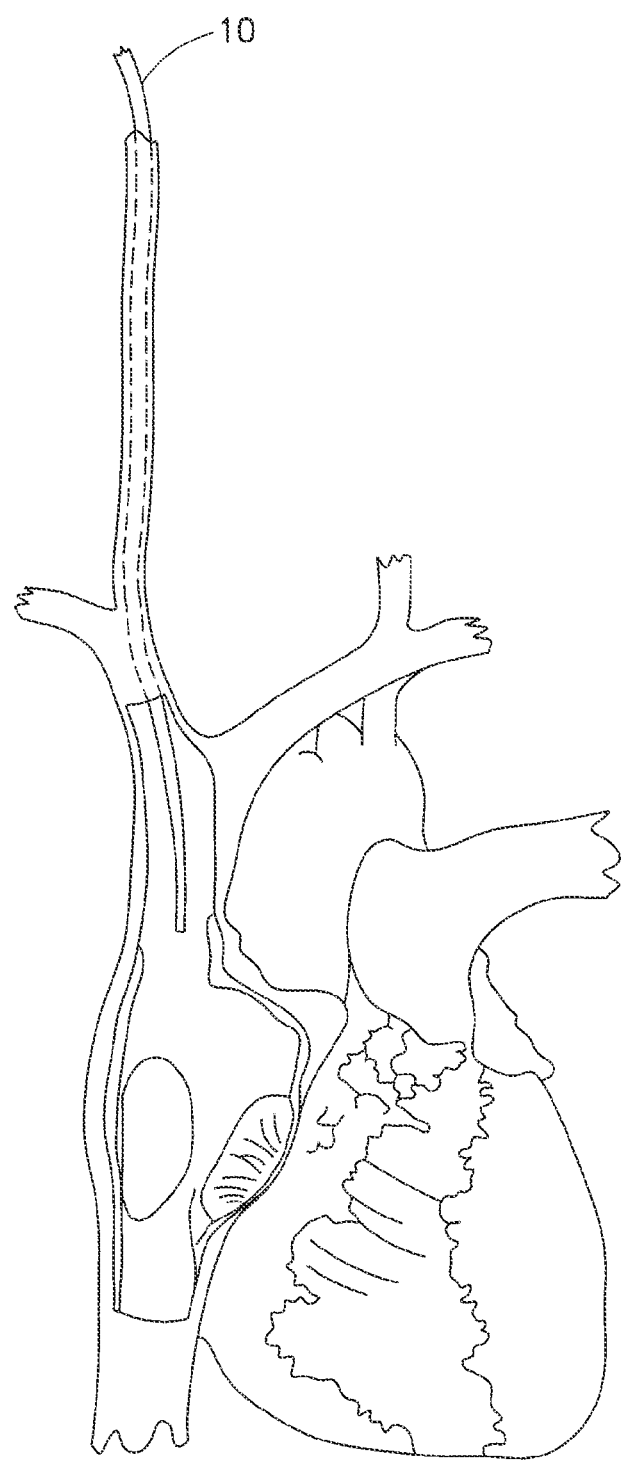
FIG. 11 is a schematic view of one embodiment of a coaxial cannula positioned in the superior vena cava of a body of a patient.
Figure 12:
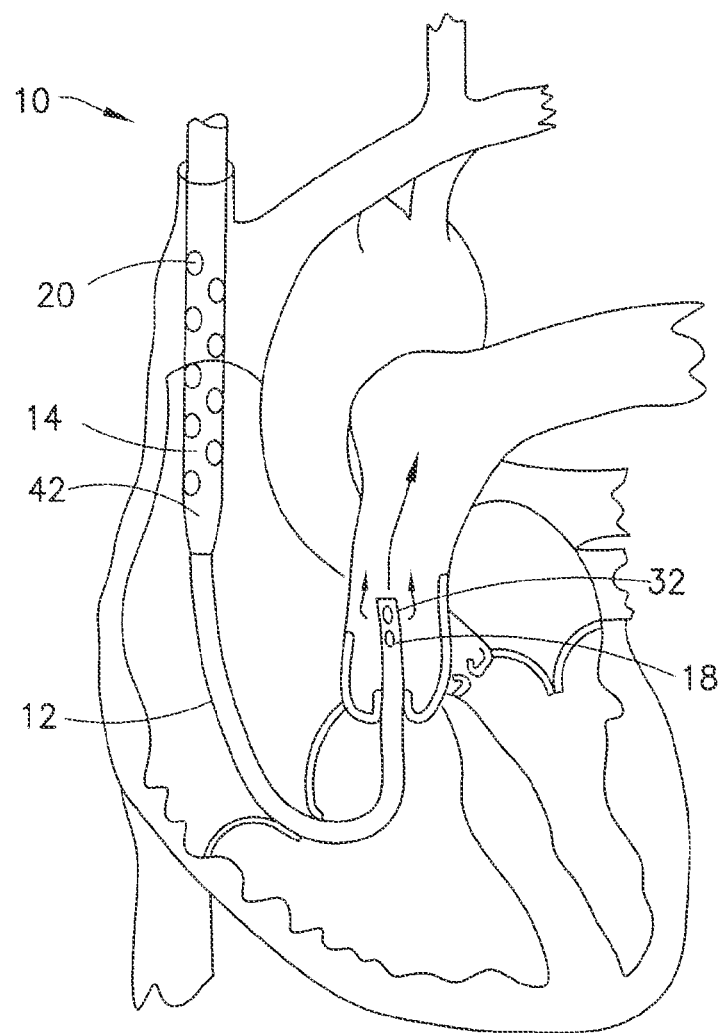
FIG. 12 is a schematic view of one embodiment of a coaxial cannula positioned inside a patient's heart.

Having described several non-limiting embodiments of the coaxial cannula 10 and the connector 22, an exemplary and non-limiting method for supporting the right heart of a patient using the coaxial cannula 10 and the connector 22 will now be described with reference to FIG. 11. In use, the coaxial cannula 10 is inserted into the pulmonary artery (PA) in a percutaneous procedure. The coaxial cannula 10 withdraws blood from the patient's heart and delivers blood back to the patient. Initially, a percutaneous entry needle (not shown) is used to access the patient's internal jugular vein (IJV). A guidewire is then inserted through the needle until the tip of the guidewire is positioned in the upper portion of the inferior vena cava/right atrium (IVC/RA) junction. The needle can then be removed and a pulmonary wedge catheter inserted over the guidewire into the PA. The guidewire tip is then threaded into the PA, and the wedge catheter is removed. The IJV is then serially dilated and the coaxial cannula 10 is threaded along the guidewire into the IJV. The introducer can be removed when the coaxial cannula 10 is in the right ventricle. The coaxial cannula 10 can then be threaded over the guidewire up into the PA. The distal end of the first infusion tube 12 is sufficiently flexible as to allow it to be easily flexed about the longitudinal axis of the first elongate body 28. The coaxial cannula 10 may include insertion depth markers and radiopaque markers for aiding the user in placing the coaxial cannula 10 in the right atrium. A curve in the coaxial cannula 10 is a feature that helps it make the turn from the right ventricle into the PA. Once the cannula's position is acceptable, the introducer/guidewire assembly is removed and the coaxial cannula 10 is clamped. The coaxial cannula 10 is secured to the patient's neck using a suture.

While several embodiments of a coaxial cannula are shown in the accompanying figures and described hereinabove in detail, other embodiments will be apparent to, and readily made by, those skilled in the art without departing from the scope and spirit of the invention.

The invention claimed is:

1. A dual lumen cannula comprising:
    a drainage tube having a proximal end, a distal end, and a lumen extending therethrough;
    an infusion tube coaxially aligned within the lumen of the drainage tube, the infusion tube having a proximal end, a distal end, and a lumen extending therethrough;
    wherein the infusion tube includes a distal end region extending distally beyond the distal end of the drainage tube to the distal end of the infusion tube;
    a plurality of drainage apertures extending through a sidewall of the drainage tube proximal of the distal end of the drainage tube, the plurality of drainage apertures including ag first group of drainage apertures longitudinally spaced apart distally from a second group of drainage apertures by a segment of the drainage tube without any drainage apertures, wherein a length of the segment of the drainage tube without any drainage apertures is greater than a distance between adjacent drainage apertures of the first group and/or the second group of drainage apertures;
    a plurality of infusion apertures extending through a sidewall of the infusion tube adjacent the distal end of the infusion tube, wherein a distal end region of the infusion tube has a tapered section extending distally beyond a distal-most aperture of the plurality of infusion apertures and to the distal end of the infusion tube; and
    a connector provided at the proximal end of the infusion tube and the proximal end of the drainage tube, the connector including an inlet portion defining an infusion fluid pathway in fluid communication with the lumen of the infusion tube and an outlet portion defining a drainage fluid pathway in fluid communication with the lumen of the drainage tube;
    wherein the infusion fluid pathway and the drainage fluid pathway transition from a coaxial arrangement at a distal end of the connector to an axially offset arrangement at a proximal end of the connector.

2. The dual lumen cannula of claim 1, wherein a distal end region of the drainage tube has a tapered portion extending distally beyond a distal-most aperture of the plurality of drainage apertures to the distal end of the drainage tube.

3. The dual lumen cannula of claim 1, wherein a total cross-sectional area of the plurality of drainage apertures is equal to or greater than a cross-sectional area of the lumen extending through the drainage tube.

4. The dual lumen cannula of claim 1, wherein the plurality of drainage apertures includes a plurality of longitudinally spaced apart groups of drainage apertures.

5. The dual lumen cannula of claim 1, wherein a total cross-sectional area of the plurality of infusion apertures is equal to or greater than a cross-sectional area of the lumen extending through the infusion tube.

6. The dual lumen cannula of claim 1, wherein the infusion tube includes a reinforcing coil.

7. The dual lumen cannula of claim 6, wherein the reinforcing coil of the infusion tube extends into the connector.

8. The dual lumen cannula of claim 7, wherein the reinforcing coil of the infusion tube extends to the distal end of the infusion tube.

9. The dual lumen cannula of claim 6, wherein the drainage tube includes a reinforcing coil.

10. The dual lumen cannula of claim 9, wherein the reinforcing coil of the drainage tube surrounds the reinforcing coil of the infusion tube.

11. The dual lumen cannula of claim 9, wherein the reinforcing coil of the drainage tube extends to the distal end of the drainage tube.

12. A dual lumen cannula comprising:
a drainage tube having a proximal end, a distal end, and a lumen extending therethrough;
an infusion tube coaxially aligned within the lumen of the drainage tube, the infusion tube having a proximal end, a distal end, and a lumen extending therethrough;
wherein the infusion tube includes a distal end region extending distally beyond the distal end of the drainage tube to the distal end of the infusion tube;
a plurality of drainage apertures extending through a sidewall of the drainage tube proximal of the distal end of the drainage tube, the plurality of drainage apertures including a first group of drainage apertures longitudinally spaced apart distally from a second group drainage apertures by a segment of the drainage tube without any drainage apertures, wherein a length of the segment of the drainage tube without any drainage apertures is greater than a distance between adjacent drainage apertures of the first group and/or the second group of drainage apertures;
a plurality of infusion apertures extending through a sidewall of the infusion tube adjacent the distal end of the infusion tube, wherein a distal end region of the infusion tube has a tapered section extending distally beyond a distal-most aperture of the plurality of infusion apertures and to the distal end of the infusion tube; and
a connector provided at the proximal end of the infusion tube and the proximal end of the drainage tube, the connector including an inlet portion defining an infusion fluid pathway in fluid communication with the lumen of the infusion tube and an outlet portion defining a drainage fluid pathway in fluid communication with the lumen of the drainage tube;
wherein the drainage tube includes a reinforcing coil extending along a length thereof and the infusion tube includes a reinforcing coil extending along a length thereof;
wherein the reinforcing coil of the drainage tube surrounds the reinforcing coil of the infusion tube.

13. The dual lumen cannula of claim 12, wherein a proximal end of the reinforcing coil of the infusion tube is located within the connector.

14. The dual lumen cannula of claim 13, wherein a proximal end of the reinforcing coil of the drainage tube is located within the connector.

15. The dual lumen cannula of claim 14, wherein the proximal end of the reinforcing coil of the infusion tube extends proximally of the reinforcing coil of the drainage tube within the connector.

16. The dual lumen cannular of claim 12, wherein a distal end region of the drainage tube has a tapered portion extending distally beyond a distal-most aperture of the plurality of drainage apertures to the distal end of the drainage tube.

17. The dual lumen cannula of claim 12, wherein a total cross-sectional area of the plurality of drainage apertures is equal to or greater than a cross-sectional area of the lumen extending through the drainage tube.

\* \* \* \* \*